(12) United States Patent
Landis et al.

(10) Patent No.: US 9,784,684 B2
(45) Date of Patent: Oct. 10, 2017

(54) METHOD FOR MANUFACTURING A SUBSTRATE FOR SURFACE-ENHANCED RAMAN SPECTOGRAPHY AND SUBSTRATE

(71) Applicant: COMMISSARIAT A L'ENERGIE ATOMIQUE ET AUX ENERGIES ALTERNATIVES, Paris (FR)

(72) Inventors: Stefan Landis, Tullins (FR); Vincent Reboud, Paris (FR)

(73) Assignee: COMMISSARIAT À L'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 109 days.

(21) Appl. No.: 14/988,165

(22) Filed: Jan. 5, 2016

(65) Prior Publication Data

US 2016/0195476 A1 Jul. 7, 2016

(30) Foreign Application Priority Data

Jan. 5, 2015 (FR) ...................... 15 50010

(51) Int. Cl.
*G01N 21/65* (2006.01)
*C23C 14/24* (2006.01)
(Continued)

(52) U.S. Cl.
CPC ........... *G01N 21/658* (2013.01); *C23C 14/24* (2013.01); *B82Y 15/00* (2013.01); *B82Y 20/00* (2013.01)

(58) Field of Classification Search
CPC ......... G01J 3/44; G01N 21/658; G01N 21/65; G01N 2021/653; G01N 2021/655; G01N 2021/656; G01N 21/01; G01N 2201/068
See application file for complete search history.

(56) References Cited

U.S. PATENT DOCUMENTS 9,632,032 B2 * 4/2017 Landis .................. G01N 21/01
2011/0109902 A1 * 5/2011 Lin ...................... G01N 21/658
356/301

(Continued)

OTHER PUBLICATIONS

Lin, T.-R., et al., "Coating effect on optical resonance of plasmonic nanobowtie antenna," Applied Physics Letters 97, 063106, 2010.
(Continued)

*Primary Examiner* — Michael A Lyons
*Assistant Examiner* — Violeta A Prieto
(74) *Attorney, Agent, or Firm* — Pillsbury Winthrop Shaw Pittman LLP (57) ABSTRACT

A substrate for surface-enhanced Raman spectography includes a support including an upper surface; a supporting structure including at least one microstructured pattern, the microstructured pattern including a top and sidewalls, with the sidewalls extending according to a direction secant to the direction of the upper surface; a multilayer arranged on the sidewalls of the microstructured pattern, with the multilayer including at least two pillar layers, separated from each other by an intermediate layer, each intermediate layer having an end set back with respect to an end of each adjacent pillar layer in such a way that the ends of two successive pillar layers form pins separated by a cavity, with the ends of the pillar layers being covered by a metal layer.

17 Claims, 9 Drawing Sheets

(51) Int. Cl.
  *B82Y 15/00* (2011.01)
  *B82Y 20/00* (2011.01)

(56) References Cited

U.S. PATENT DOCUMENTS

| | | |
|---|---|---|
| 2011/0140209 A1 | 6/2011 | Wang et al. |
| 2011/0305994 A1* | 12/2011 | Montelius ................. G03F 1/54 430/322 |
| 2013/0038870 A1 | 2/2013 | Lin et al. |
| 2016/0195475 A1* | 7/2016 | Landis .................. G01N 21/01 356/244 |

OTHER PUBLICATIONS

Ou, F.S., et al., "Hot-Spot Engineering in Polygonal Nanofinger Assemblies for Surface Enhanced Raman Spectroscopy," Nano Letters 2011, 11, pp. 2538-2542.
Choi, S., et al., "Ultradense gold nanostructures fabricated using hydrogen silsesquioxane resist and applications for surface-enhanced Raman spectroscopy," Journal of Vacuum Science & Technology B 27, pp. 2640-2643, 2009.
Zhang, Z., et al., "Manipulating Nanoscale Light Fields with the Asymmetric Bowtie Nano-Colorsorter," Nano Letters, vol. 9, No. 12, 2009, pp. 4505-4509.
French Search Report as issued in French Patent Application No. 1550010, dated Jul. 23, 2015.
Seol, M.-L., et al., "Multi-layer nanogap array for high-performance SERS substrate," Nanotechnology, vol. 22, No, 23, (2011), 5 pages.

\* cited by examiner

METHOD FOR MANUFACTURING A SUBSTRATE FOR SURFACE-ENHANCED RAMAN SPECTOGRAPHY AND SUBSTRATE

CROSS-REFERENCE TO RELATED APPLICATIONS

This application claims priority to French Patent Application No. 1550010, filed Jan. 5, 2015, the entire content of which is incorporated herein by reference in its entirety.

FIELD

The field of the invention is that of methods for manufacturing substrates that can be used to implement methods of surface-enhanced Raman spectography (SERS). The invention also relates to a substrate for surface-enhanced Raman spectography.

BACKGROUND

Surface-enhanced Raman spectography (SERS) is one of the most promising detection techniques for identifying and characterising molecules. This technique consists in depositing the molecules of interest on a substrate that has a rough metal surface. The metal surface whereon the molecules of interest are fixed is then illuminated by a monochromatic light. The molecules then emit a Raman signal characteristic of these molecules, which makes them able to be detected and identified.

However the Raman signal emitted by the molecules has an intensity that is much less than the intensity of the monochromatic light with which the molecules were illuminated.

In order to overcome this problem, it has been observed that the roughness of the metal surface of the substrate that carries the molecules of interest makes it possible to enhance the Raman signal emitted by the molecules of interest thanks to the excitation of localised plasmons of the metal (enhancement via electromagnetic effect) and by transfer of charges between the metal and the molecule adsorbed (chemical effect). This enhancement makes it possible as such to specifically detect adsorbed samples with extremely low concentrations and/or over very short periods of time.

This enhancement can be accomplished thanks to "hot spots". These hot spots are zones of the substrate where the electromagnetic field is localised and intense. For this, hot spots generally have dimensions that are less than the wavelength of the incident monochromatic light.

Prior art as such knows methods that make it possible to carry out hot spots on the surface of a substrate. These hot spots can be formed by cavities or by point effects. As such, the document Appl. Phys. Lett. 97, 063106 2010, Nanoletters, 9, 4505, 2009 describes hot spots formed by points. The document Nano Lett. 11, 2538, 2011; J. Vac. Sci. Technol. B 27, 2640 (2009) describes hot spots formed by cavities. However, the methods for forming hot spots of prior art use structuring technologies that can reach very high spatial resolutions and they are therefore complex and very expensive. Furthermore, they do not generally make it possible to produce substrates that have a high density of hot spots, in such a way that the increase in the light intensity emitted by the molecules of interest is limited.

SUMMARY

An aspect of the invention aims to overcome the disadvantages of prior art by proposing a method for manufacturing a substrate for surface-enhanced Raman spectography that is easy to implement, and which allows for a constant increase in the light intensity emitted by the molecules over the whole of the substrate.

Another aspect of the invention is to propose a method for manufacturing a substrate for surface-enhanced Raman spectography that can be reproduced and that is reliable, that allows for a substantial increase in the light intensity emitted by the molecules of interest and which has a high density of hot spots.

Another aspect of the invention is to propose a method for manufacturing a substrate for surface-enhanced Raman spectography that makes it possible to simultaneously carry out a large number of identical substrates.

To do this, a first aspect of the invention relates to a method for manufacturing a substrate for surface-enhanced Raman spectography, with the method comprising the following steps:

(a) creating a supporting structure on an upper surface of a support, with the supporting structure comprising at least one microstructured pattern, with the microstructured pattern comprising a top and sidewalls, with the sidewalls extending according to a direction secant to the direction of the upper surface;

(b) depositing a multilayer on the supporting structure, with the multilayer comprising at least two layers of a first dielectric material, referred to as "pillar layers", separated from one another by a layer of a second dielectric material, referred to as "intermediate layer", the second dielectric material that can be selectively etched in relation to the first dielectric material;

(c) etching of a portion of the multilayer deposited on the top of the microstructured pattern in such a way as to expose an end of each layer of the multilayer;

(d) selective etching of a portion of each end of each intermediate layer in such a way as to form cavities between the ends of two successive pillar layers;

(e) depositing a metal layer on each end of each pillar layer.

As such, this method proposes to carry out in a first step a supporting structure of which the dimensions, typically between 50 nm and 100 µm, do not make it directly possible to obtain the enhancement function of the electromagnetic field, but which is easy to carry out by known techniques. On this supporting structure, other structures are then carried out with characteristic dimensions that are much smaller which this time make it possible to enhance the electromagnetic field. These second structures are carried out by successive deposits of layers made of two different dielectric materials of which one can be selectively etched with respect to the other in such a way as to form a multilayer that hugs the shape of the supporting structure. A clipping is then carried out locally of the portion of the multilayer deposited on the upper portion of each pattern of the supporting structure. The alternating of the layers of the multilayer is then exposed to air in such a way that there is access to each one of the ends of the layers of the multilayer. The ends of the intermediate layers of the multilayer can then be selectively and partially etched in such a way as to form cavities between the ends of two successive pillar layers. The method then comprises a step of depositing a metal layer on each one of the ends of the pillar layers. This step of functionalising the end of the pillar layers with a metal layer makes it possible to form hot spots making it possible to enhance the Raman signal emitted by the molecules of interest which will be deposited on the surface of the substrate thanks to an electromagnetic coupling effect between two successive metal layers. The metal layers deposited on the ends of the pillar layers are also called "metal pins" in what follows.

The method is particularly beneficial as it makes it possible to easily carry out metal pins of nanometric dimensions separated by cavities of nanometric dimensions without resorting to aggressive etching methods. Furthermore, the width of the metal pins and of the cavities is controlled very well since it is determined by the thickness of the layers deposited. This thickness is easy to control.

The method then makes it possible to easily obtain a substrate that allows for a reinforcing of the electromagnetic field. The intensity of the electromagnetic field obtained thanks to the substrate formed as such can as such be between 10 times and several thousands of times greater than that obtained with the substrates of prior art.

The method according to an embodiment the invention can also have one or several of the characteristics hereinafter taken individually or according to any technically permissible combination.

In an embodiment, the method further comprises a step of depositing a metal layer on each end of each intermediate layer. This step therefore makes it possible to deposit a metal layer at the bottom of each cavity formed between two successive metal pins since the bottom of each cavity is formed by the end of an intermediate layer. This step allows for a reinforcing of the electromagnetic field since as such not only a coupling is established between the metal layers deposited on the ends of two successive pillar layers but also between a metal layer deposited on the end of a pillar layer and the metal layer deposited on the end of the intermediate layer that is adjacent to it.

In an embodiment, the layers of the multilayer are deposited according to a compliant depositing technique. This compliant depositing technique is in an embodiment a heat treatment in a high-temperature ultra-vacuum oven, also called TTH.

In an embodiment, during the step of depositing a metal layer on each end of each pillar layer, the metal layer can be deposited by one of the following techniques: physical vapour deposition (PVD), vacuum evaporation, or by electrolysis.

In an embodiment, each microstructured pattern has a height between 50 nm and 100 µm, which makes it possible to easily manufacture the microstructured pattern with the known methods.

In an embodiment, each layer of the multilayer has a thickness between 1 angstrom and 100 nm, and for example between 10 nm and 50 nm. The thickness of the layers of the multilayer will condition the width of the metal pins and those of the cavities between these picots.

In an embodiment, the multilayer has a thickness less than the height of the microstructured pattern, which makes it possible to update all of the layers during the step (c) of etching of the portion of the multilayer deposited on the top of the microstructured patterns.

In an embodiment, the sidewalls of the microstructured pattern extend according to a direction that forms an angle strictly less than 90° with a direction normal to the upper surface of the support, which makes it possible to carry out compliant deposits more easily on the microstructured pattern.

In an embodiment, the supporting structure is carried out in such a way as to form a photonic crystal with respect to an incident wave illuminating the substrate.

In an embodiment, the supporting structure is carried out in such a way that the sidewalls of the microstructured pattern comprise faces separated from each other by edges, the angle of these edges being chosen in such a way that the supporting structure, once covered by the multilayer, generates a reinforcing of the electromagnetic field via the point effect in zones located in the vicinity of the edges.

According to various embodiments, the etching of a portion of the multilayer deposited on the top of the microstructured pattern can be carried out by chemical mechanical planarisation or by dry etching.

A second aspect of the invention relates to a substrate for surface-enhanced Raman spectography comprising:
 a support comprising an upper surface;
 a supporting structure arranged on the upper surface of the support, with the supporting structure comprising at least one microstructured pattern, with the microstructured pattern comprising a top and sidewalls, with the sidewalls extending according to a direction secant to the direction of the upper surface;
 a multilayer arranged on the sidewalls of the microstructured pattern, with the multilayer comprising at least two layers of a first dielectric material, referred to as "pillar layers", separated from one another by a layer of a second dielectric material, referred to as "intermediate layer", the second dielectric material that can be selectively etched in relation to the first dielectric material, with each intermediate layer having an end that is set back with respect to one end of each adjacent pillar layer in such a way that the ends of two successive pillar layers form pins separated by a cavity, with the ends of the pillar layers being covered by a metal layer.

Such a substrate comprises multiple hot spots between successive metal layers whereon is formed an electromagnetic coupling, which makes it possible to substantially enhance the Raman signal emitted by the molecules of interest deposited on this substrate thanks to the excitation of localised plasmons of the metal (enhancement via electromagnetic effect). Such a substrate therefore makes it possible to increase the light intensity emitted by molecules of interest which are deposited on its surface in such a way that it allows for a faster detection of these molecules of interest.

The substrate according to the second aspect of the invention can have one or several of the characteristics hereinafter taken individually or according to any technically permissible combination.

In an embodiment, the sidewall of the microstructured pattern comprises faces separated by edges, which makes it possible to create a reinforcement of the electromagnetic field via the point effect and therefore to increase the enhancement of the Raman signal emitted by the molecules.

In an embodiment, the supporting structure comprises several microstructured patterns forming a periodic array, which makes it possible to increase the density of hot spots on the surface of the substrate, and to homogenise their distribution on the substrate. The enhancement of the Raman signal generated by the substrate is as such more substantial and more homogeneous.

In an embodiment, the end of each intermediate layer is also covered with a metal layer which makes it possible to increase the electromagnetic coupling created and therefore the increase in the light intensity emitted by molecules of interest which are deposited on its surface in such a way that it allows for a faster detection of these molecules of interest.

In an embodiment, the metal layer deposited on the end of an intermediate layer is separated from the metal layer deposited on the end of the pillar layer adjacent to this intermediate layer which makes it possible to reduce the reflectivity of the substrate formed as such and therefore which makes it possible to trap the light by forming a cavity of the Perot Fabry type and as such increase the enhancement via the electromagnetic effect obtained.

In an embodiment, the metal layer deposited on the end of an intermediate layer is separated from the metal layer deposited on the end of the pillar layer adjacent to this intermediate layer by a distance between 1 nm and 40 nm, and for example between 10 nm and 30 nm, which makes possible an optimum increase of the enhancement via the electromagnetic effect obtained.

According to an embodiment, the supporting structure is dimensioned in such a way as to form a photonic crystal with respect to an incident wave illuminating this substrate. The photonic crystal therefore makes it possible to redirect the incident light in a direction parallel to the plane of the substrate. As such, when the incident wave arrives on the substrate, it will be coupled in the plane of the substrate, in such a way that the light intensity emitted by molecules of interest which are deposited on its surface are as such further increased. This substrate therefore makes it possible to further increase the rapidity of detecting the molecules of interest.

According to an embodiment, the supporting structure is dimensioned in such a way as to form a wave guide arranged to facilitate the extraction of a Raman signal emitted by molecules deposited on the surface of the substrate.

In an embodiment, each microstructured pattern has a height between 50 nm and 100 μm.

In an embodiment, each layer of the multilayer has a thickness between 1 angstrom and 50 nm, for example between 10 nm and 50 nm.

In an embodiment, each cavity has a depth between 1 angstrom and 200 nm, and for example between 10 nm and 100 nm.

BRIEF DESCRIPTION OF THE FIGURES

Other characteristics and benefits of the invention shall appear when reading the following detailed description, in reference to the annexed figures, which show:

FIGS. 1c', 1d' and 1e', steps alternative to the steps shown respectively in the FIGS. 1c, 1d, 1e;

FIG. 3b, an enlarged view of the portion E of the substrate of FIG. 3a;

FIG. 8a, a representation of the level of reflectivity according to the period of the supporting structure and of the incident wavelength for w1, w2 and h1 on the substrate of FIG. 7a;

DETAILED DESCRIPTION

FIGS. 1a to 1g show the various steps of a method according to an embodiment of the invention.

Figure 1A:
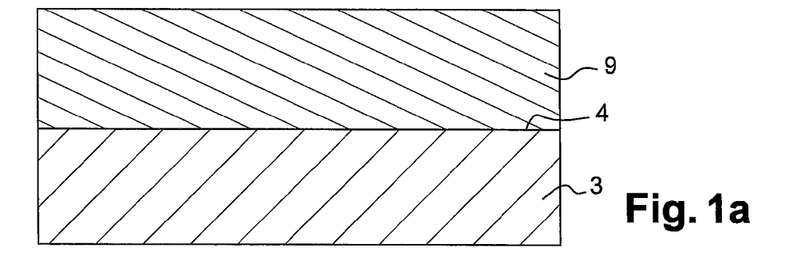
FIGS. 1a to 1g, the steps of a method according to an embodiment of the invention.

This method comprises a first step 101 of carrying out a supporting structure 2 on an upper surface 4 of a support 3. According to various embodiments, the support 3 can be made of silicon, metal, glass. Moreover, the upper surface 4 can be covered by a layer of silicon oxide.

The supporting structure 2 comprises at least one microstructured pattern 5, and in an embodiment several microstructured patterns 5. Each microstructured pattern has in an embodiment dimensions between 50 nm and 100 μm. Each microstructured pattern 5 has an upper portion 8, also referred to as "top" or "crest", and a sidewall 7, also referred to as "slope". The sidewall 7 of the microstructured patterns 5 extends in an embodiment according to a direction secant to the upper surface 4 of the support 3. The microstructured patterns 5 can have different shapes.

Figure 1B:
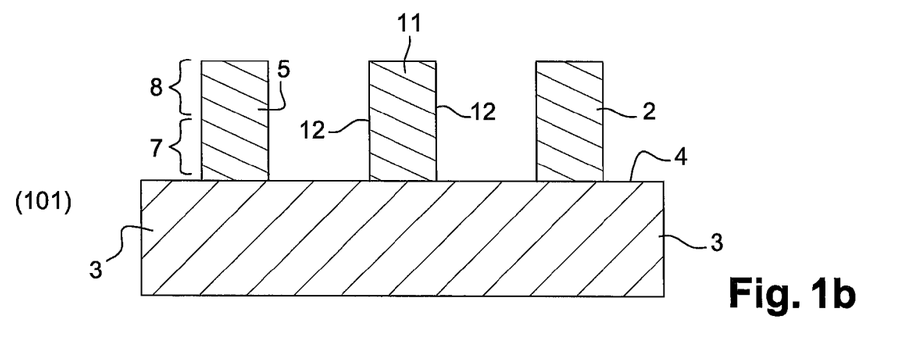

As such, according to an embodiment shown in FIG. 1b, each microstructured pattern 5 can have a parallelepiped shape. In this case, each microstructured pattern 5 comprises:

an upper wall 8 extending according to a direction substantially parallel to the upper surface 4 of the support;
a sidewall 7 extending according to a direction substantially perpendicular to the upper surface 4 of the support 3. The sidewall 7 comprises four faces 11 separated from each other by edges 12.

Figure 2A:
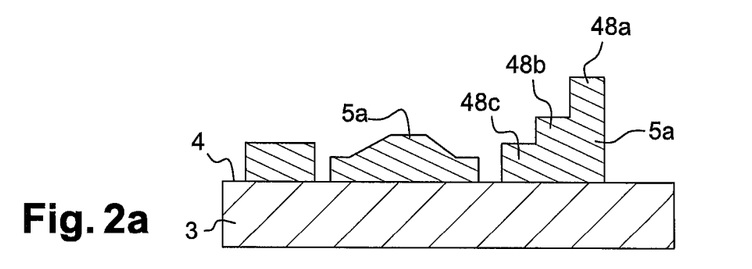
FIGS. 2a and 2b, supporting structures that can be used in a method according to an embodiment of the invention.
Figure 2B:
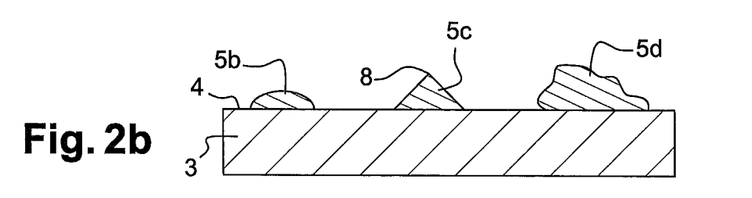

However, the microstructured patterns could also have other shapes. As such in reference to FIG. 2a, each microstructured pattern 5a could comprise several portions 48a, 48b, 48c, having heights that are different from one another. A microstructured pattern is then obtained 5a which has the shape of a staircase. In reference to FIG. 2b, each microstructured pattern 5b could have a dome shape, or a triangle shape, pyramid shape, or more complex shapes. According to various embodiments, the microstructured patterns of the supporting structure can all have the same shape, as shown in FIG. 1b, or they can have different shapes, as shown in FIGS. 2a and 2b.

The supporting structure 2 is in an embodiment constituted of a dielectric material. It can for example be constituted of silicon nitride or silicon oxide. According to an embodiment, the supporting structure is constituted of polymers. Indeed, polymers have the benefit of not absorbing or absorbing very little of the plasmonic resonance of metals, in such a way that they do not reduce the enhancement of the local electromagnetic field. According to various embodiments, the supporting structure can be constituted of polymers with an acrylic base, of polymers with a poly hydroxy styrene (PHS) base or polymers with a methyl methacrylate (MMA) base. Polymers with an acrylic base make it possible to have a better mechanical resistance for the subsequent steps of the method.

The supporting structure 2 can be carried out thanks to various techniques according to the material that it is formed from. As such, in reference to FIGS. 1a and 1b, when the supporting structure is made of polymer, the step of carrying out the supporting structure can comprise the following substeps:

forming of a layer of polymer 9 on the upper surface 4 of the support 3, for example via spin-coating;
formation of the microstructured patterns 5, for example via nanoimprint lithography, photolithography, electronic lithography, extreme ultraviolet lithography, interferential lithography or laser inscription.

Figure 1C:
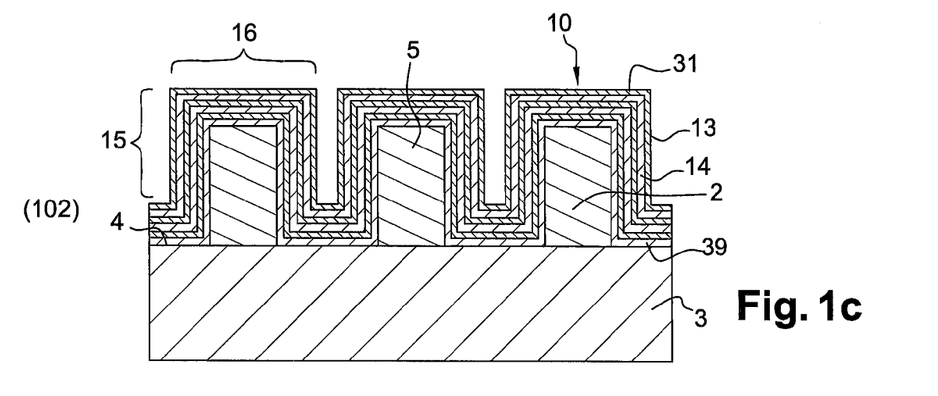

In reference to FIG. 1c, the method then comprises a step 102 of depositing a multilayer 10 on the supporting structure 2. The multilayer 10 hugs the shape of the supporting structure 2 in such a way that it is deposited on the upper portion 8 of the microstructured patterns 5 and on their sidewall 7. The multilayer 10 therefore comprises portions 15 that extend according to a direction secant to the upper surface 4 of the support and other portions 16 that extend according to a direction substantially parallel to the upper surface 4 of the substrate.

The multilayer 10 comprises at least two layers 13 of a first dielectric material. The layers 13 of the first dielectric materials are called "pillar layers" 13. Two successive pillar layers 13 are separated from each other by an intermediate layer 14 into a second dielectric material. The second dielectric material is chosen in such a way as to be able to be selectively etched in relation to the first dielectric material. Moreover, the first and the second dielectric materials are chosen in such a way that they do not absorb or absorb very little the plasmon generated by the substrate. The first and the second dielectric materials are in an embodiment chosen from among the following materials: silicon oxide, alumina, hafnium oxide, silicon nitride, titanium oxide.

Each layer 13, 14 of the multilayer has in an embodiment a thickness between 1 nm and 100 nm.

The layers of the multilayer are in an embodiment deposited by a compliant depositing method in such a way that the thickness of the multilayer is substantially the same over the entire surface of each microstructured pattern. A heat deposit under ultra vacuum and at high temperature, an EVAP deposit, or a deposit via spraying with the target inclined and rotating substrate can for example be used for this.

During the step of depositing the multilayer, the first layer deposited on the microstructured patterns, which shall be called "inside layer" 39, can be a pillar layer or this can be an intermediate layer. Likewise, the last layer deposited, which shall be called "outside layer" 31, can be a pillar layer or this can be an intermediate layer.

Figure 1D:
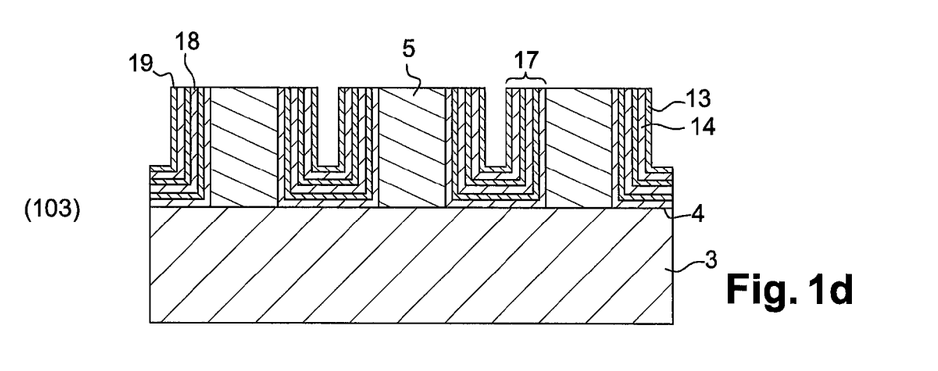

In reference to FIG. 1d, the method then comprises a step 103 of etching a portion 16 of the multilayer deposited on the upper portion 8 of each microstructured pattern 5. This step 103 is referred to as "step of clipping". Indeed, it comprises a step of etching the portion 16 of the multilayer deposited on the crest 8 of each one of the microstructured patterns 5. This step 103 can also comprise a step of etching of a portion of the crest 8 of each microstructured pattern 5. In the embodiment of FIG. 1d, the portion 16 of the multilayers deposited on the upper surface 8 of the microstructured patterns 5 is etched. For this, the regions of the multilayers which are parallel to the upper surface 4 of the support can for example be etched, while etching slower the regions 15 of the multilayer which are inclined with respect to the upper surface 4 of the support. A spacer patterning technique can be used for this. This step of etching 103 can also be carried out by chemical mechanical planarisation (CMP).

Columns 17 are thus obtained at the end of this step 103 extending according to a direction secant to the upper surface 4 of the support 3, with each column 17 comprising an alternating of pillar layers 13 and of intermediate layers 14. The upper ends 18 of each pillar layer 13 and the upper ends 19 of each intermediate layer 14 are exposed to the air and they can therefore be accessed for the rest of the steps of the method.

Figure 1E:
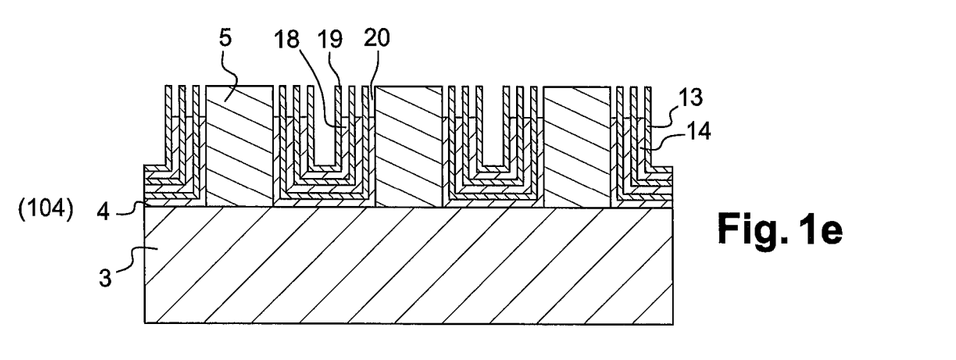

In reference to FIG. 1e, the method then comprises a step 104 of selective etching of a portion of the ends 18 of the intermediate layers 14 in such a way as to form cavities of air 20 between the ends 19 of two successive pillar layers 13. More precisely, during this step, the ends 18 of the intermediate layers 14 are selectively etched in relation to the ends 19 of the pillar layers 13 in such a way that, at the end of this step, the ends 19 of the metal layers are separated by cavities of air 20. This step of etching is partial in such a way as to retain a portion of the intermediate layers 14 between the pillar layers 13, which makes it possible to maintain the pillar layers 13 in place without them collapsing on one another and also to have cavities of air 20 of a controlled depth. The technique used to selectively etch the intermediate layers depends on the material chosen for the intermediate layers 14 and for the pillar layers 13. According to various embodiments, the technique chosen can be a dry or wet etching technique.

Figure 1F:
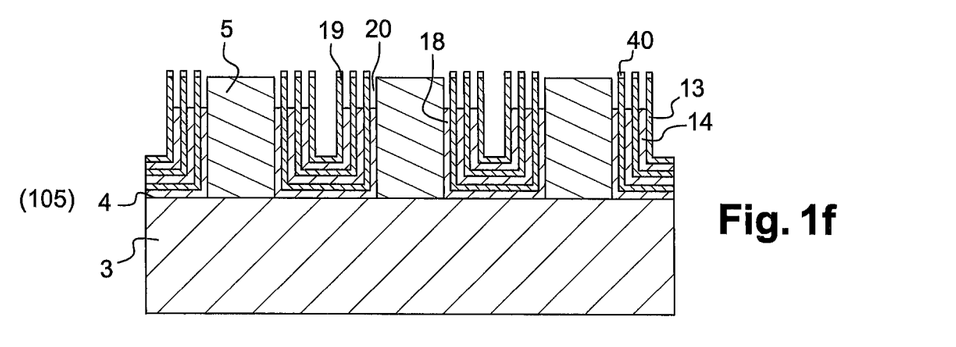

In reference to FIG. 1*f*, the method then comprises a step 105 of depositing a metal layer 40 on each end 19 of each pillar layer 13. This metal layer can for example be made of gold, silver, copper in aluminium, copper or an alloy of these materials. The metal layer could also be constituted of Ni, Ti, TiN or an alloy of these materials. This step of depositing can be carried out by a technique of physical vapour deposition, evaporation, or by electrolysis. These metal layers 40 deposited on the ends 19 of the pillar layers 13 are also called "metal pins". The metal layers 40 allow for a localised reinforcing of the electromagnetic field when they are subjected to an incident electromagnetic radiation of a predefined wavelength.

The method makes it possible to manufacture a substrate thanks to which the light intensity emitted by molecules of interest which are deposited on its surface is enhanced. The substrate formed as such therefore allows for a faster detection of the molecules of interest which are deposited on its surface.

Figure 1G:
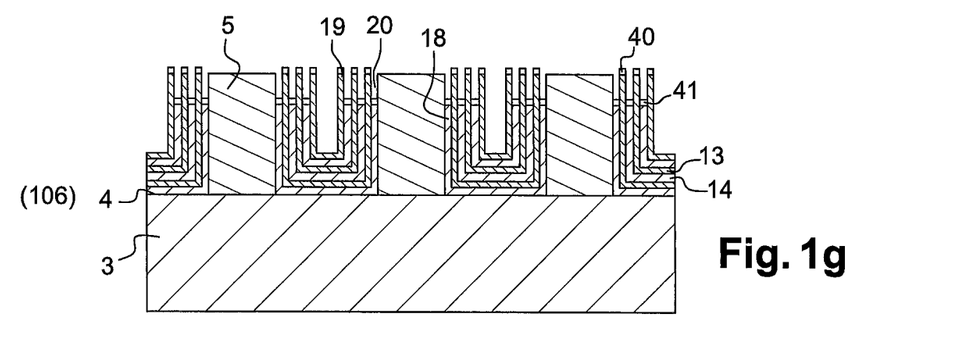

In reference to FIG. 1*g*, the method can also comprise a step 106 of depositing a metal layer 41 on the end 18 of the intermediate layers 14. This metal layer 41 is in an embodiment constituted of the same material as the one that constitutes the metal layer 40 deposited on the ends 19 of the pillar layers. The metal layers deposited on the intermediate layers have in an embodiment the same thickness as the metal layers 40 deposited on the pillar layers.

At the end of this step, metal layers 40 are thus obtained both on the ends of the pillar layers and at the bottom of the cavities that separate the ends 19 of two successive pillar layers. The metal layers 41 deposited on the ends of the intermediate layers are in an embodiment separated from the metal layers 40 deposited on the ends of the pillar layers in order to optimise the reinforcing of the electromagnetic field as shall be seen in what follows. The step 106 of depositing metal layers 41 on the intermediate layers is in an embodiment simultaneous to the step 105 of depositing metal layers 40 on the pillar layers.

The method can then comprise a step of depositing molecules of interest on the surface of the substrate obtained as such. The molecules of interest are then deposited on the surface of the metal pins and in the cavities of air. The materials chosen to carry out the supporting structure can be chosen according to their surface energy, in such a way as to control the depositing of the molecules which will then be deposited on the substrate. The depositing of molecules at certain locations of the substrate rather than at other locations can as such be favoured.

The invention is not limited to the embodiment described hereinabove. As such, as shown in FIGS. 1*c'* to 1*e'*, the method described in reference to FIGS. 1*a* to 1*f* could also comprise, following the step 102 of depositing of the multilayer 10, an additional step 102*b* is of depositing a dielectric material 27 in the spaces 28 formed between the microstructured patterns 5 covered by the multilayer 10. This dielectric material 27 makes it possible to fill in the empty space 28 between the microstructured patterns 5 which makes the step of clipping 103 easier and more controllable. Moreover, as this empty space 28 is filled in, the residues formed during the step 103 of clipping will not be lodged in the empty space 28 in such a way that they can subsequently be easily removed by surface cleaning methods. In the opposite case removing these residues can be impossible or very complicated and the latter could disturb the proper operation of the substrate. The dielectric material 27 deposited in the spaces 28 can be for example silicon oxide or silicon nitride. The later steps 103 to 106 of the method are identical to those described hereinabove.

The method according to an embodiment of the invention is particularly beneficial since it makes it possible to obtain metal pins 40 separated by cavities with dimensions that can be precisely controlled. Indeed, the width w1 of the metal pins 40 obtained is controlled by controlling the thickness of the metal layers 13 deposited. Likewise, the width w2 of the cavities of air is controlled by controlling the thickness of the intermediate layers 14 deposited. The width of the pins and of the cavities can therefore be controlled easily and precisely since the thickness of the layers deposited is also as such. Moreover, the depth of the cavities of air can be controlled by controlling the etching of the end of the intermediate layers 20 which it too is also easy to control. Furthermore, since the intermediate layer is made of dielectric material, the method does not use a step of aggressive etching since the intermediate layer can easily be etched by dry or chemical etching.

Dimensioning of the Metal Pins and of the Cavities:

A method for dimensioning the metal layers 40 deposited on the pillar layers and metal layers 41 deposited on the intermediate layers shall now be described in reference to FIGS. 3*a*, 3*b*, 4, 5 and 6.

Figure 3A:
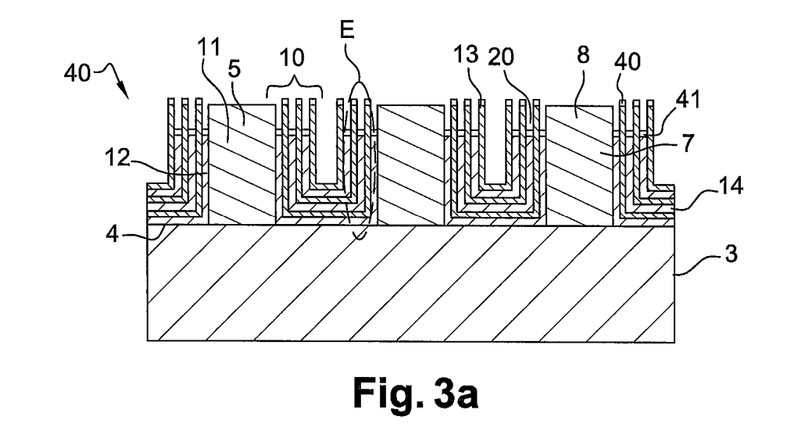
FIG. 3a, a diagrammatical representation of a substrate according to an embodiment of the invention.
Figure 3B:
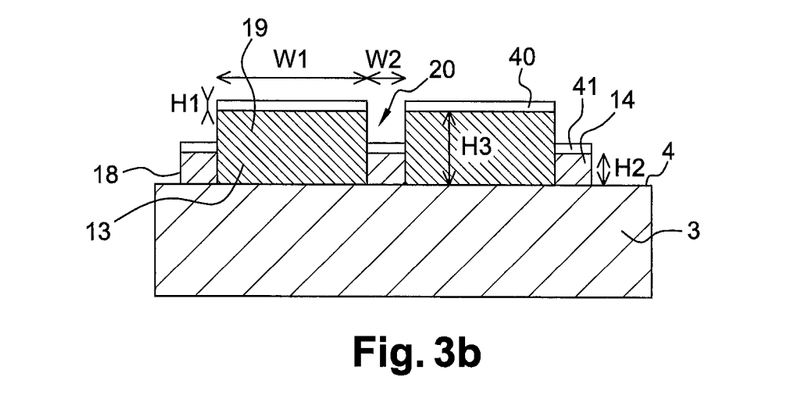

In reference to FIG. 3*b*, each pillar layer 13 has a thickness w1 and a height H3. Each intermediate layer 14 has a thickness w2 and a height H2. The end of each pillar layer and the end of each intermediate layer are covered by a metal layer 40, respectively 41, with a thickness H1. The distance between the metal layer 40 deposited on a pillar layer and the metal layer 41 deposited on the intermediate layer adjacent to this pillar layer is given by H3−(H1+H2).

The dimensions w1, w2, H1, H2 and H3 are chosen in such a way as to minimise the reflectivity of the substrate for a given incident wavelength and to maximise the reinforcing of the electromagnetic field.

For this, the length of the incident wave of the monochromatic light that will be sent on the molecules to be detected are chosen first. This incident wavelength can be chosen according to the molecules to be detected and/or according to the equipment available to the user. In this embodiment, an incident wavelength of 785 nm for example is chosen.

The materials that will constitute the pillar layers 13 and the intermediate layers 14 are then chosen. This choice can be dictated by technological motivations, in particular by the methods available for depositing these layers, and by the methods available for selectively etching the material constituting the intermediate layers in relation to the pillar layers. This choice can also be carried out according to the chemical affinities of the materials with the molecules to be detected, and/or according to the adsorption properties of the materials chosen with regards to the incident wavelength. In this embodiment, it is chosen for example to carry out the pillar layers in $Si_3N_4$ and the intermediate layers in $SiO_2$.

The materials that will constitute the metal layers 40 and the metal layers 41 are then chosen. These materials can be chosen according to the methods of depositing available, and/or for reasons of chemical affinities with the molecules to be detected, and/or according to the absorption properties of these materials with regards to the incident wavelength. In this embodiment, it is chosen for example to carry out metal layers 40 and 41 made of gold.

Simulations are then carried out in order to determine the dimensions w1, w2, H1, H2 and H3 that minimise the reflectivity of the substrate and that maximise the electromagnetic field locally.

A method called RCWA (rigorous coupled wave analysis) or a method called FDTD for "finite difference time domain" can for example be used for this. These methods make it possible to simulate the reflectivity of a surface according to its geometry and its composition.

Figure 4A:
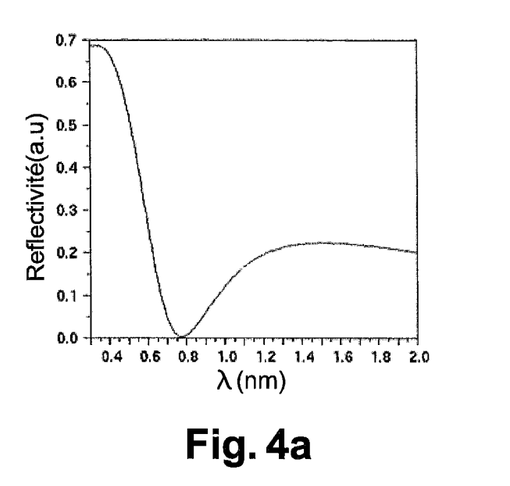
FIG. 4a, a curve showing the change in the reflectivity according to the wavelength of the incident light on a substrate according to an embodiment of the invention comprising metal pins with a width W1=40 nm and with a thickness H1=30 nm, with two metal pins being separated by an intermediate layer with a width W2=15 nm and with a height H2=45 nm, with the metal pins being deposited on a pillar layer with a height H3=145 nm.
Figure 4B:
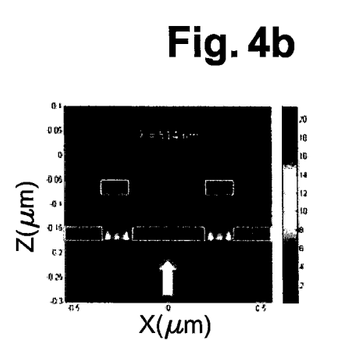
FIGS. 4b and 4c, the electromagnetic field on the substrate of FIG. 4a, calculated respectively at 514 nm and at 785 nm.
Figure 4C:
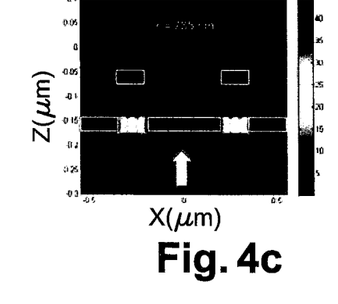

As such, FIG. 4a shows the change in the reflectivity of the substrate of FIGS. 3a and 3b according to the incident wavelength. The substrate has the following dimensions: w1=40 nm; w2=15 nm; H1=30 nm; H2=45 nm; H3=145 nm. FIG. 4b shows the electromagnetic field calculated on this substrate as a response to an incident wave with a wavelength of 514 nm. FIG. 4c shows the electromagnetic field maximal calculated on this substrate as a response to an incident wave with a wavelength of 785 nm.

Figure 5:
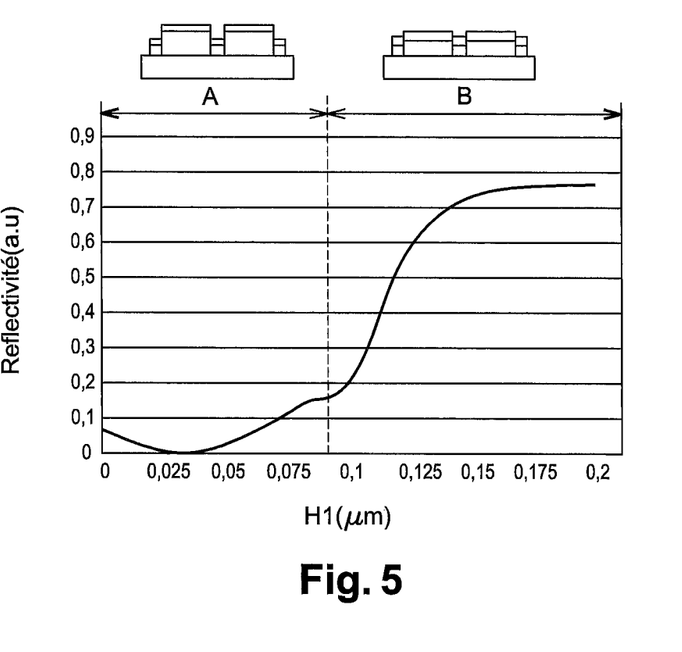
FIG. 5, a curve showing the reflectivity of a first substrate A and of a second substrate B according to two embodiments of the invention, for an incident wavelength of 785 nm, according to the height H1 of the metal pins of these substrates, when these substrates have the following dimensions: W1=40 nm, W2=15 nm, H2=45 nm, H3=145 nm.

In reference to FIG. 5, it can be seen that the thickness H1 of the metal layers 40 and 41, and the distance H3-H1-H2 between these metal layers 40, 41, also plays a role in the improving of the electromagnetic field local. Indeed, FIG. 5 shows the reflectivity of a substrate A and of a substrate according to the thickness H1 of the metal layers 40 and 41, for an incident wave with a wavelength of 785 nm. The substrate A is such as the one shown in FIGS. 3a and 3b and it has:

adjacent metal layers 40 and 41 which are separated;
dimensions w1=40 nm, w2=15 nm, H2=45 nm, H3=145 nm.

The substrate B is identical to the substrate A except that the metal layers 40 and 41 are not separated, i.e. a metal layer 40 touches the metal layer 41 that is adjacent to it.

As can be seen in FIG. 5, it is desirable to have separated metal layers 40 and 41 in such a way as to have a minimum of reflectivity and a maximum of electromagnetic field locally. Furthermore, the reflectivity is minimum for a thickness H1 of the metal layers 40 and 41 equal to 0.03 µm.

Figure 6:
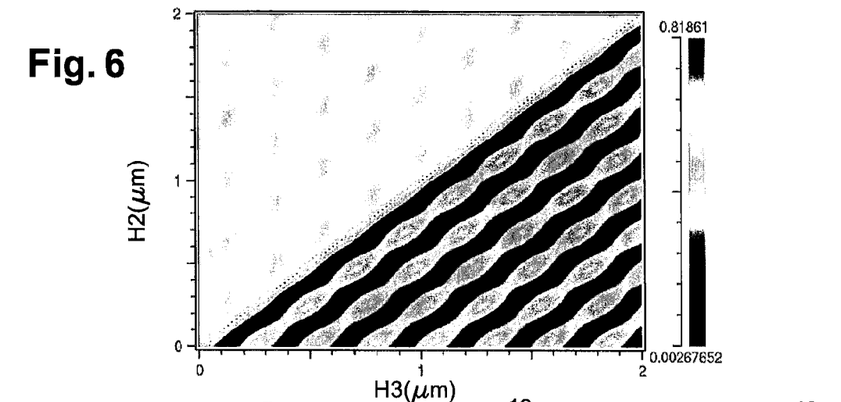
FIG. 6, a diagram showing the change in the reflectivity of a substrate according to an embodiment of the invention for an incident wavelength of 785 nm, according to the dimensions H2 and H3 of this substrate with W1 set to 40 nm, W2 set to 15 nm, H1 set to 30 nm.

FIG. 6 shows the change in the reflectivity for a substrate similar to the one in FIG. 3b according to H2 and H3 in the presence of an incident wave at 785 nm, when w1=40 nm, w2=15 nm, H1=30 nm. As can be seen in this figure, substantial changes in resonance take place according to H2 and H3.

These simulations therefore make it possible to determine:

the thickness w1 of the pillar layers deposited;
the width w2 of the intermediate layers deposited;
the thickness H1 of the metal layers deposited;
the height H3 of the pillar layers deposited;
the height H2 of the intermediate layers deposited.

Moreover, according to the anisotropies of the technique of depositing, the thickness w1, w2 of the pillar and intermediate layers deposited can be adjusted so as to offset this depositing anisotropy. Indeed, knowing this depositing anisotropy, the correction to be made to the thicknesses w1 and w2 can be calculated in order to optimise the final shape of the substrate obtained.

Simulations can also be carried out in order to determine the number of layers in the multilayer. These simulations are identical to those shown hereinabove except that instead of taking into consideration only two pillar layers and one intermediate layer, a larger number of layers is taken into consideration in such a way as to identify or not modes of coupling between the various repetitions of layers, which may or may not modify the optimal geometries somewhat. The optimum thickness of the multilayer 10 is as such deduced from this.

Figure 7A:
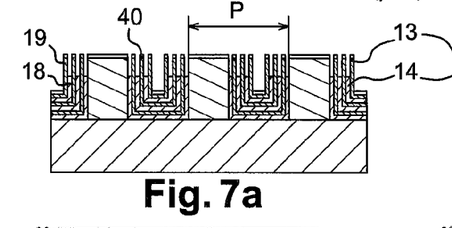
FIG. 7a, a diagrammatical cross-section view of a substrate according to an embodiment of the invention comprising a metal layer on the end of the pillar layers.
Figure 7B:
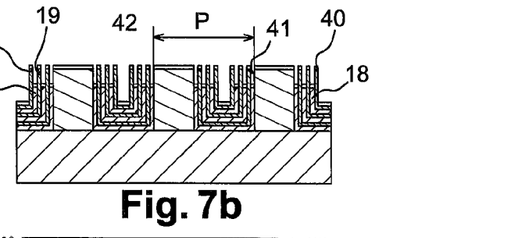
FIG. 7b, a diagrammatical cross-section view of a substrate according to another embodiment of the invention comprising a metal layer on the end of the pillar layers and a metal layer on the end of the intermediate layers.
Figure 8A:
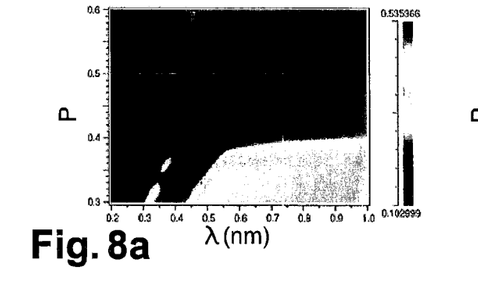
Figure 8B:
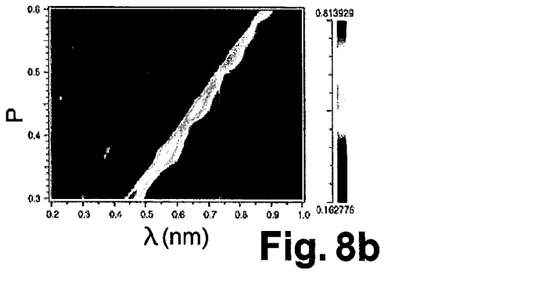
FIG. 8b, a representation of the level of reflectivity according to the period of the supporting structure and of the incident wavelength for w1, w2 and h1 on the substrate of FIG. 7b.

It can also be chosen to deposit metal layers 40 only on the pillar layers 13 as shown in FIG. 7a, or it can be chosen to deposit metal layers 40 and 41 both on the pillar layers 13 and on the intermediate layers 14 as shown in FIG. 7b. FIG. 8a shows a mapping of the reflectivity of the substrate of FIG. 7a according to the wavelength of the incident wave and of the period P of the supporting structure. The minimums for reflectivity correspond to the maximums for the enhancement of the electromagnetic field on the supporting structure. FIG. 8b shows a mapping of the reflectivity of the substrate of FIG. 7b according to the wavelength of the incident wave and of the period P of the supporting structure. As can be seen in these figures, the presence of a metal layer both on the end of the pillar layers and on the end of the intermediate layers makes it possible to substantially improve the electromagnetic field at the incident wavelength for which the substrate was dimensioned.

In reference to FIGS. 7b and 8b, it is beneficial to carry out a resonating optical cavity 42 formed by the metal layer 40 deposited on the end of the pillar layers 13 and by the metal layer 41 deposited on the end of the intermediate layers 14. The presence of this cavity 42 substantially increases the coupling of the Raman pump in the substrate.

Figure 9:
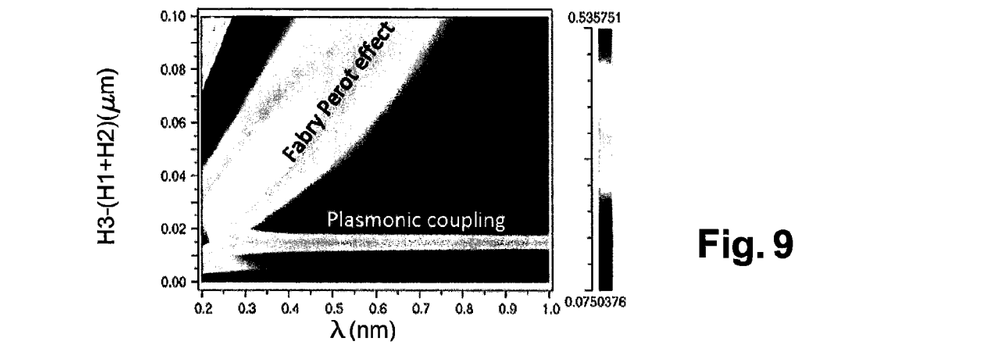
FIG. 9, a mapping of the coupling of the Raman pump according to the wavelength and the distance between the metal layer deposited on the end of the pillar layers, and that deposited on the end of the intermediate layers.

As can be seen in FIG. 9, the coupling force of the Raman pump depends on the distance H3-(H1+H2) between the metal layer 40 deposited on the pillar layers and the metal layer 41 deposited on the intermediate layers. When this distance H3-(H1+H2) is equal to 20 nm, it is observed that a strong coupling of the Raman pump in the substrate is obtained. The more the distance H3-(H1+H2) increases, the weaker the coupling is. It is therefore beneficial to have a distance H3-(H1+H2) between the metal layer 40 deposited on a pillar layer and the metal layer 41 deposited on the adjacent intermediate layer less than 40 nm, and in an embodiment at 30 nm, while still keeping the metal layer 40 deposited on a pillar layer separate from the metal layer 41 deposited on the adjacent intermediate layer.

Dimensioning of the Microstructured Patterns:

In reference to FIGS. 10a, 10b, 11a, 11b, the method comprises a step of determining the dimensions of the microstructured patterns of the supporting structure. The choice of these dimensions does not necessarily require a calculation of the reinforcing of the electromagnetic waves, outside of the height of these patterns which is determined in such a way as to have the height H3 sought for the pillar layers. The other dimensions of the microstructured patterns are in an embodiment determined according to:

the technological capacity of the methods used to carry out these patterns during the step 101;
the technological capacity of the etching methods used during the step 103;
the technological capacity of the depositing methods for their ability to planarise an existing structure if the thickness deposited is excessive. Indeed, if the microstructured patterns are too high, it is more complicated to have a compliant deposit over the entire height of each pattern as each step of depositing, in particular if it is carried out by PVD or evaporation, is not perfectly compliant and there is a slight deformation in the shape of the resulting structure after each deposit and therefore as the deposit takes place there can be a planarisation of the structure which is not sought.

Figure 10A:
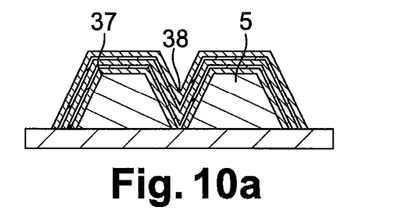
FIGS. 10a and 10b, views of a substrate according to an embodiment of the invention during a method of carrying out this substrate.
Figure 10B:
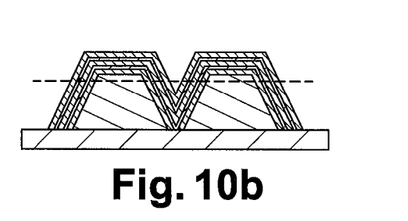
Figure 11A:
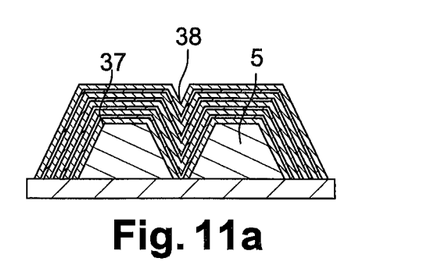
FIGS. 11a and 11b, views of a substrate according to another embodiment during a method of carrying out this substrate.
Figure 11B:
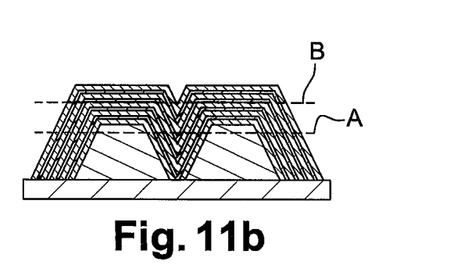
Figure 12A:
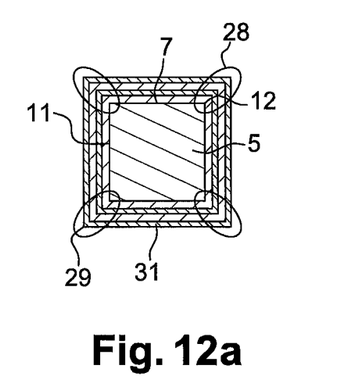
FIGS. 12a and 12b, top views of substrates according to two embodiments of the invention.
Figure 12B:
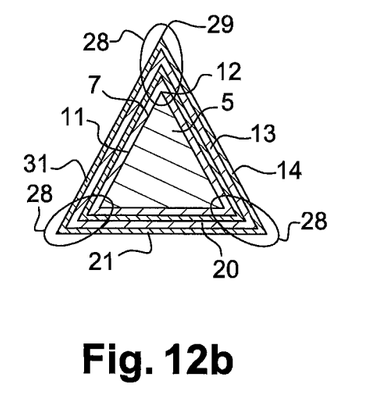

Moreover, in reference to FIGS. 10a and 10b, the height of the microstructured patterns 5 is in an embodiment chosen in such a way that after depositing of the multilayer the highest point 37 of the first layer deposited will be higher than the lowest point 38 of the last layer deposited. As such, after the step 103 of clipping, all of the layers of the multilayer will be updated. In the opposite case, shown in FIGS. 11a and 11b, a portion of the layers of the multilayer will not be able to be used for the manufacture of the cavities, since:

either they will be entirely suppressed during the step of clipping. This is the case if the clipping is done according to the line A;

or they will not be used at all because they are entirely covered by other layers. This is the case if the clipping is done according to the line B.

The shape of each microstructured pattern 5 can also be determined by simulating the response that the substrate will have according to the shape chosen. These simulations can also be carried out with a rigorous coupled wave analysis method or a finite difference time domain method. As such, in reference to FIGS. 12a, 12b, 13a, 13b, the shape of the sidewalls 7 of the microstructured patterns 5 is in an embodiment chosen in such a way that the sidewalls 7 comprise faces 11 separated from each other by edges 12. The angle of these edges 12 is determined in such a way that the supporting structure, once covered by the multilayer 10, generates a reinforcing of the electromagnetic field via the point effect in zones 28 located in the vicinity of the edges 12. Indeed, it is then the metal layers deposited on the edges 12 that will generate a point effect.

Figure 13A:
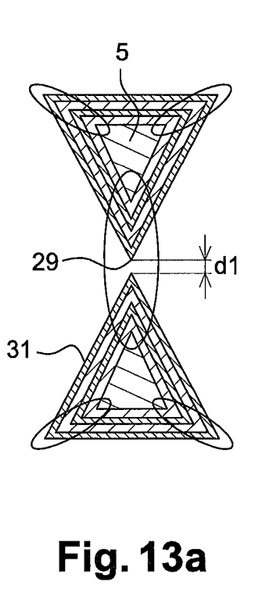
FIGS. 13a and 13b, top views of substrates according to two other embodiments of the invention.
Figure 13B:
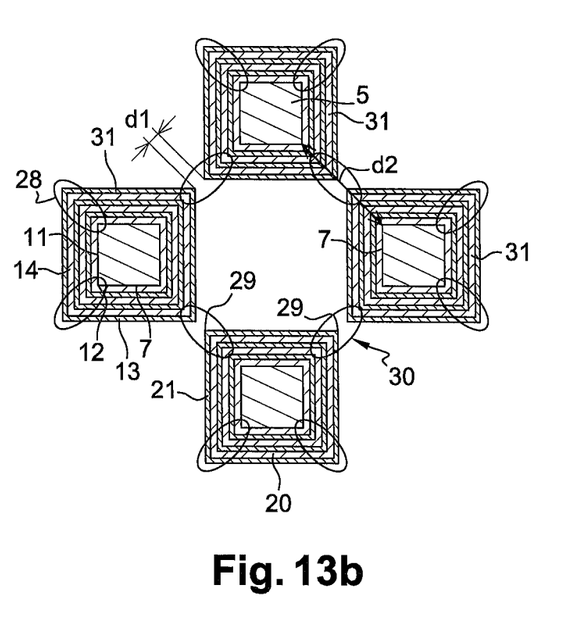

Moreover, in reference to FIGS. 13a and 13b, the separation between two adjacent microstructured patterns can also be determined, by simulations with electromagnetic calculation software, in such a way as to optimise the coupling effects between adjacent microstructured patterns in such a way as to increase the reinforcing of the electromagnetic field. More precisely, by optimising the distance between the edges 29 of the outside layer 31 that surround two adjacent microstructured patterns, the reinforcing of the electromagnetic field can be optimised further by coupling the point effect generated by the metal layers 40 or 41 located on the ends of the edges 29. The confinement of the electromagnetic field created in the space 30 formed between these two edges 29 is as such optimised. This optimisation of the distance d1 between the edges 29 of the outer metal layer 31 is in an embodiment carried out thanks to an electromagnetic calculation software. This distance d1 is in an embodiment between 1 nm and 50 nm. Once the distance d1 is set, as the thickness of the multilayer 10 was set hereinabove during the step of dimensioning the cavities and the pins, the distance d2 between the edges 12 of two adjacent microstructured patterns 5 is deduced from this.

Choice of the Arrangement of the Supporting Structure:

The method also comprises a step of determining the arrangement of the supporting structure.

Figure 14A:
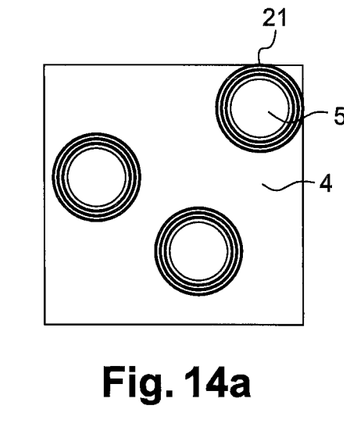
FIGS. 14a and 14b, top views of substrates according to a first and a second embodiment of the invention.
Figure 14B:
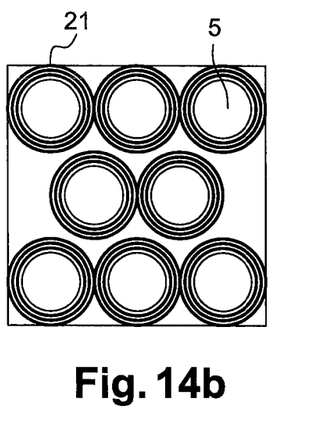

The supporting structure, in an embodiment, comprises several microstructured patterns 5 on which the multilayer will be deposited. These microstructured patterns 5 can be isolated from one another as shown in FIG. 14a or they can form an array as shown in FIG. 14b. Having microstructured patterns that form an array makes it possible to have a greater density of hot spots.

Moreover, in the case where the microstructured patterns form an array, the periodicity P of the array formed can be chosen in such a way as to optimise the amplification of the electromagnetic field emitted according to the incident wavelength for which the substrate is dimensioned. Indeed, as shown in FIGS. 8a and 8b, the electromagnetic field varies according to the periodicity of the supporting structure.

The supporting structure is in an embodiment dimensioned in such a way as to form at least one photonic crystal with respect to the incident wave sent on the substrate, which makes it possible to increase the effectiveness of the coupling of the metal layers with the incident light and therefore increase the Raman signal. The supporting structure can form a photonic crystal since the layers of the multilayer are made of a dielectric. Furthermore, the support and the supporting structure are also made of dielectric materials. In this embodiment, the support 3 is in an embodiment made of silicon and it is, in an embodiment, covered with a layer of silicon oxide. The supporting structure is in an embodiment constituted of silicon nitride.

FIGS. 17a to 17d show examples of geometries of photonic crystals respectively with a square, hexagonal, or honeycomb geometry and random able to be used to carry out the supporting structure.

Figure 15A:
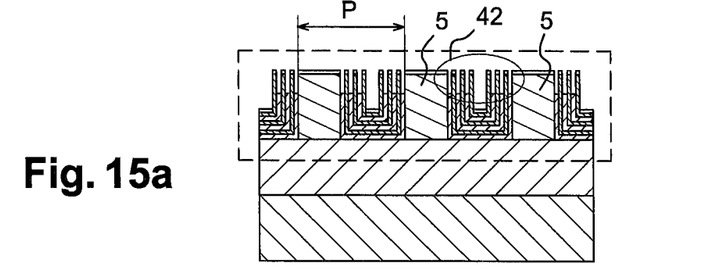
FIG. 15a, a side view of a substrate according to an embodiment of the invention forming a wave guide for the Raman signal emitted by the molecules of interest deposited on said substrate.
Figure 15B:
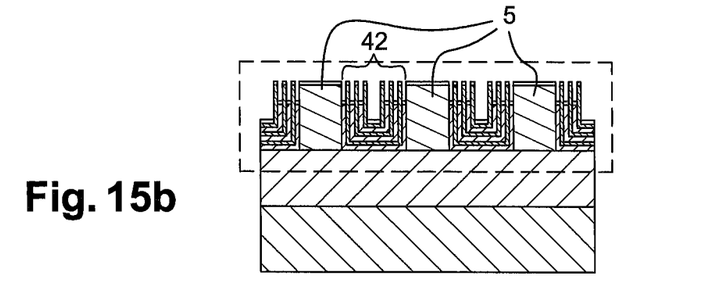
FIG. 15b, a side view of a substrate according to an embodiment of the invention forming an extraction array for the Raman signal emitted by the molecules of interest deposited on said substrate.

FIGS. 15a and 15b show a substrate according to an embodiment of the invention. In this embodiment, the supporting structure is dimensioned in such a way as to form resonating cavities 42 with respect to the incident wave sent on the substrate. More precisely, in FIG. 15a, the photonic crystal is dimensioned to couple the incident wave in the plane of the substrate.

In FIG. 15b, the photonic crystal 42 is dimensioned to extract the Raman signal emitted by the molecules of interest outside of the plane of the substrate. In this embodiment, the supporting structure is therefore dimensioned in such a way as to form a wave guide that makes it possible to extract the Raman signal emitted by the molecules deposited on the surface of the substrate. The geometry of the photonic crystals formed by the supporting structure is such that the light emitted by the molecules deposited on the surface of the substrate is diffracted perpendicularly to the surface 4 of the substrate, i.e. at the point P of the diagram of the band calculated by a wave-basis frequency domain method as shown in FIG. 16.

The supporting structure therefore makes it possible to facilitate the extraction of the Raman signal emitted by the molecules outside of the substrate, in such a way that the substrate makes it possible to facilitate the detecting of the molecules which are adsorbed on its surface.

Figure 16:
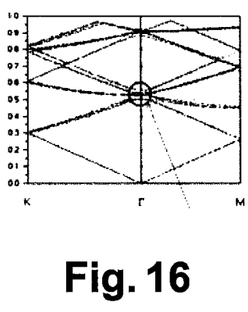
FIG. 16 a diagram of the bands of a photonic crystal formed by the substrate of FIG. 13b, with this diagram being calculated by a plane wave-basis frequency-domain method.
Figure 17A:
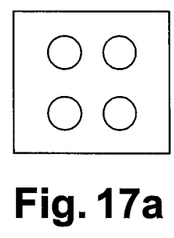
FIGS. 17a to 17d, examples of geometries of photonic crystals that can be used within the framework of an embodiment of the invention.
Figure 17B:
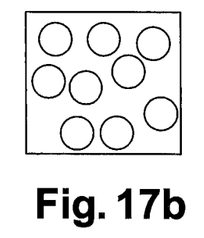
Figure 17C:
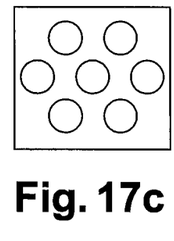
Figure 17D:
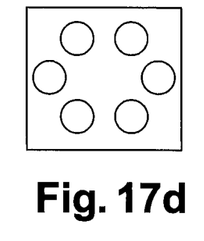

As such, using the band diagram of FIG. 16, the supporting structure can form a photonic crystal with a hexagonal geometry that has a period of 430 nm and a reduced frequency of 0.55. Greater periods can also be used generating a more substantial emission annular diagram and therefore a microscope objective with a wider digital opening can be used, such as for example geometries of holes in a high index layer, these geometries able to be hexagonal, a honeycomb, square or random with an average period of 430 nm.

Naturally, the invention is not limited to the embodiments described in reference to the figures and alternatives can be considered without leaving the scope of the invention.

The invention claimed is:

1. A method for manufacturing a substrate for surface-enhanced Raman spectography, the method comprising:

creating a supporting structure on an upper surface of a support, with the supporting structure comprising at least one microstructured pattern, the microstructured pattern comprising a top and sidewalls, with the sidewalls extending according to a direction secant to a direction of the upper surface;

depositing a multilayer on the supporting structure, with the multilayer comprising at least two pillar layers of a first dielectric material separated from one another by an intermediate layer of a second dielectric material, the second dielectric material being selectively etchable in relation to the first dielectric material;

etching a portion of the multilayer deposited on the top of the microstructured pattern in such a way as to expose an end of each layer of the multilayer;

selective etching a portion of each end of each intermediate layer in such a way as to form cavities between the ends of two successive pillar layers;

depositing a metal layer on each end of each pillar layer.

2. The method according to claim 1, further comprising depositing a metal layer on each end of each intermediate layer.

3. The method according to claim 2, wherein, during the depositing of a metal layer on each end of each pillar layer, the metal layer is deposited by one of the following techniques: physical vapour deposition (PVD), vacuum evaporation, or by electrolysis.

4. The method according to claim 1, wherein the layers of the multilayer are deposited according to a compliant depositing technique.

5. The method according to claim 1, wherein the etching of a portion of the multilayer deposited on the top of the microstructured pattern is carried out by chemical mechanical planarisation.

6. The method according to claim 1, wherein the supporting structure is carried out in such a way as to form a photonic crystal with respect to an incident wave illuminating the substrate.

7. The method according to claim 1, wherein the supporting structure is carried out in such a way that the sidewalls of the microstructured pattern comprise faces separated from each other by edges, an angle of the edges being chosen in such a way that the supporting structure, once covered by the multilayer, generates a reinforcing of an electromagnetic field via the point effect in zones located in a vicinity of the edges.

8. The method according to claim 1, wherein each microstructured pattern has a height between 50 nm and 100 µm.

9. The method according to claim 1, wherein each layer of the multilayer has a thickness between 1 angstrom and 100 nm.

10. The method according to claim 9, wherein each layer of the multilayer has a thickness between 10 nm and 50 nm.

11. The method according to claim 1, wherein the multilayer has a thickness less than a height of the microstructured pattern.

12. The method according to claim 11, wherein the sidewalls of the microstructured pattern extend according to a direction that forms an angle strictly less than 90° with a direction normal to the upper surface of the support.

13. A substrate for surface-enhanced Raman spectography comprising:

a support comprising an upper surface;

a supporting structure arranged on the upper surface of the support, with the supporting structure comprising at least one microstructured pattern, the microstructured pattern comprising a top and sidewalls, with the sidewalls extending according to a direction secant to a direction of the upper surface, the supporting structure:

being dimensioned in such a way as to form a photonic crystal with respect to an incident wave illuminating the substrate and/or being such that the sidewalls of the microstructured pattern comprise faces separated from each other by edges, an angle of the edges being chosen in such a way that the supporting structure, once covered by the multilayer, generates a reinforcing of the electromagnetic field via the point effect in zones located in the vicinity of the edges;

a multilayer arranged on the sidewalls of the microstructured pattern, with the multilayer comprising at least two pillar layers of a first dielectric material separated from one another by an intermediate layer of a second dielectric material, the second dielectric material that being selectively etchable in relation to the first dielectric material, each intermediate layer having an end set back with respect to an end of each adjacent pillar layer in such a way that the ends of two successive pillar layers form pins separated by a cavity, with the ends of the pillar layers being covered by a metal layer.

14. The substrate according to claim 13, wherein the end of each intermediate layer is also covered with a metal layer.

15. The substrate according to claim 13, wherein the metal layer deposited on the end of an intermediate layer is separated from the metal layer deposited on the end of the pillar layer adjacent to this intermediate layer.

16. The substrate according to claim 15, wherein the metal layer deposited on the end of an intermediate layer is separated from the metal layer deposited on the end of the pillar layer adjacent to this intermediate layer by a distance between 1 nm and 40 nm.

17. The substrate according to claim 16, wherein the distance is between 10 nm and 30 nm.

* * * * *